United States Patent [19]

Barsomian et al.

[11] Patent Number: 4,983,522

[45] Date of Patent: Jan. 8, 1991

[54] METHOD FOR PRODUCING THE HINPI RESTRICTION ENDONUCLEASE AND METHYLASE

[75] Inventors: Janet M. Barsomian, Georgetown; Geoffrey G. Wilson, Boxford, both of Mass.

[73] Assignee: New England Biolabs, Inc., Beverly, Mass.

[21] Appl. No.: 134,235

[22] Filed: Dec. 17, 1987

[51] Int. Cl.$^5$ .................. C12N 15/52; C12N 9/22; C12N 1/21

[52] U.S. Cl. .................. 435/172.3; 435/199; 435/252.33; 435/320; 536/27; 935/29; 935/73; 935/80; 935/82

[58] Field of Search .................. 435/172.3, 199, 320, 435/252.3, 252.33; 935/29, 73, 80, 82; 536/27

[56] References Cited

FOREIGN PATENT DOCUMENTS 0193413 3/1986 European Pat. Off. .
0248678 9/1987 European Pat. Off. .

OTHER PUBLICATIONS

Greene, P. J. et al., (1981) J. Biol. Chem. 256(5), 2143–2153.
Newman, A. K. et al., (1981) J. Biol Chem. 256(5), 2131–2139.
Schoner, B. et al., (1983) Gene 24, 227–236.
Walder, R. Y. et al., (1984) J. Biol. Chem. 259(12), 8015–8026.
Wilson, G. G. (1988) Trends in Genetics 4(11), 314–318.
Wilson, G. G. (1988) Gene 74, 281–289.
Lunner, K. D. et al., (1988) Gene 74, 25–32.
Mann et al., Gene 3:97–112 (1978).
Kosykh et al., Molec gen. Genet. 178:717–718 (1980).
Walder et al., Proc. Nat. Acad. Sci. U.S.A., 78:1503–1507 (1981).
Bougueleret et al., Nucleic Acids Res. 12:3659–3676 (1984).
Gingeras and Brooks, Proc. Natl. Acad. Sci. U.S.A., 80:402–406 (1983).
Theriault and Roy, Gene 19:355–359 (1982).
Blumenthal et al., J. Bacteriol. 164:501–509 (1985).
Kiss et al., Nucleic Acids Res. 13:6403–6421 (1985).
Szomolanyi et al., Gene 10:219–225 (1980).
Janulaitis et al., Gene 20:197–204 (1982).
Kiss and Baldauf, Gene 21:111–119 (1983).
Walder et al., J. Biol. Chem. 258:1235–1241 (1983).
Raleigh and Wilson, Proc. Natl. Acad. Sci. U.S.A., 83:9070–9074 (1986).
Shen et al., Science Sin. 23:1435–1442 (1980).
Birnboin and Doly Nucleic Acids Res. 7:1513 (1979).

*Primary Examiner*—Elizabeth C. Weimar
*Assistant Examiner*—Charles L. Patterson, Jr.
*Attorney, Agent, or Firm*—Gregory D. Williams; David G. Conlin

[57] ABSTRACT

The present invention is directed to a method for cloning and producing the HinPI restriction endonuclease by (1) introducing the restriction endonuclease gene from *Haemophilus influenza* P1 into a host whereby the restriction gene is expressed; (2) fermenting the host which contains the vector encoding and expressing the HinPI restriction endonuclease, and (3) purifying the HinPI restriction endonuclease from the fermented host which contains the vector encoding and expressing the HinPI restriction endonuclease activity.

10 Claims, 3 Drawing Sheets

METHOD FOR PRODUCING THE HINPI RESTRICTION ENDONUCLEASE AND METHYLASE

BACKGROUND OF THE INVENTION

The present invention relates to clones for the HinPI restriction endonuclease and modification methylase, and to the production of these enzymes from the clones.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Over one hundred different restriction endonucleases have been identified among many hundreds of bacterial species that have been examined to date.

Bacteria usually possess only a small number restriction endonucleases per species. The endonucleases are named according to the bacteria from which they are derived Thus, the species *Haemophilus aegyptius*, for example synthesizes 3 different restriction endonucleases, named HaeI, HaeII and HaeIII. These enzymes recognize and cleave the sequences (AT)GGCC(AT), PuGCGCPy and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecule and cleaving them each time that the recognition sequence occurs. The disintegration that results inactivates many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$ Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones (HhaII: Mann et al., Gene 3: 97-112, (1978); EcoRII: Kosykh et al., Molec. gen. Genet 178: 717-719, (1980); PstI: Walder et al., Proc. Nat. Acad. Sci. 78 1503-1507, (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., Nucl. Acid. Res. 12:3659-3676, 1984; PaeR7: Gingeras and Brooks, Proc. Natl. Acad. Sci. USA 80:402-406, 1983; Theriault and Roy, Gene 19:355-359 1982; PvuII: Blumenthal et al., J. Bacteriol. 164:501-509, 1985).

A third approach, and one that is being used to clone a growing number of systems, involves selecting for an active methylase gene referring to our Patent application No.: 707079 (BsuRI: Kiss et al., Nucl. Acid. Res. 13:6403-6421, 1985). Since restriction and modification genes tend to be closely linked, clones containing both genes can often be isolated by selecting for just the one gene. Selection for methylation activity does not always yield a complete restriction-modification system however, but instead sometimes yields only the methylase gene (BspRI: Szomolanyi et al., Gene 10:219-225, (1980); BcnI: Janulaitis et al, Gene 20: 197-204 (1982); BsuRI: Kiss and Baldauf, Gene 21: 111-119, (1983); and MspI: Walder et al., J. Biol. Chem. 258:1235-1241, (1983)).

A potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease. Another obstacle to cloning restriction-modification systems lies in the discovery that some strains of *E. coli* react adversely to cytosine modification; they possess systems that destroy DNA containing methylated cytosine (Raleigh and Wilson, Proc. Natl. Acad. Sci., USA 83:9070-9074, 1986). Cytosine-specific methylase genes cannot be cloned easily into these strains, either on their own, or together with their corresponding endonuclease genes. To avoid this problem it is necessary to use mutant strains of *E. coli* (McrA⁻ and McrB⁻) in which these systems are defective.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

In accordance with the present invention there is provided a clone containing the genes for the HinPI restriction endonuclease and modification methylase derived from *Haemophilus influenza* P1, as well as related methods for the production of the enzymes. More specifically, this invention relates to clones which express the restriction endonuclease HinPI, an enzyme which recognizes the DNA sequence GCGC and cleaves between the first G and C; refer to Shen, S., Li, Q., Yan, P., Zhou, B., Ye, S., Lu, Y. and Wang, D. Science Sin. 23: 1435–1442 (1980), the disclosure of which is hereby incorporated by reference herein. HinPI restriction endonuclease produced in accordance with the present invention is substantially pure and free of the contaminants normally found in HinPI preparations made by conventional techniques, such as that disclosed by Shen et al., supra.

The preferred method for cloning this enzyme comprises forming a library containing the DNA from *Haemophilus influenza* P1, isolating those clones which contain DNA coding for the HinPI modification methylase and screening among these to identify those that also contain the HinPI restriction endonuclease gene.

DETAILED DESCRIPTION OF THE INVENTION

The present invention relates to clones of the HinPI restriction and modification genes, as well as to the restriction endonuclease HinPI produced from such clones. The HinPI genes are cloned by a method which takes advantage of the fact that certain clones which are selected on the basis of containing and expressing the HinPI modification methylase gene also contain the HinPI restriction gene. The DNA of such clones is resistant to digestion, in vitro, by the HinPI restriction endonuclease. This resistance to digestion affords a means for selectively isolating clones encoding the HinPI methylase and restriction endonuclease.

Figure 1:
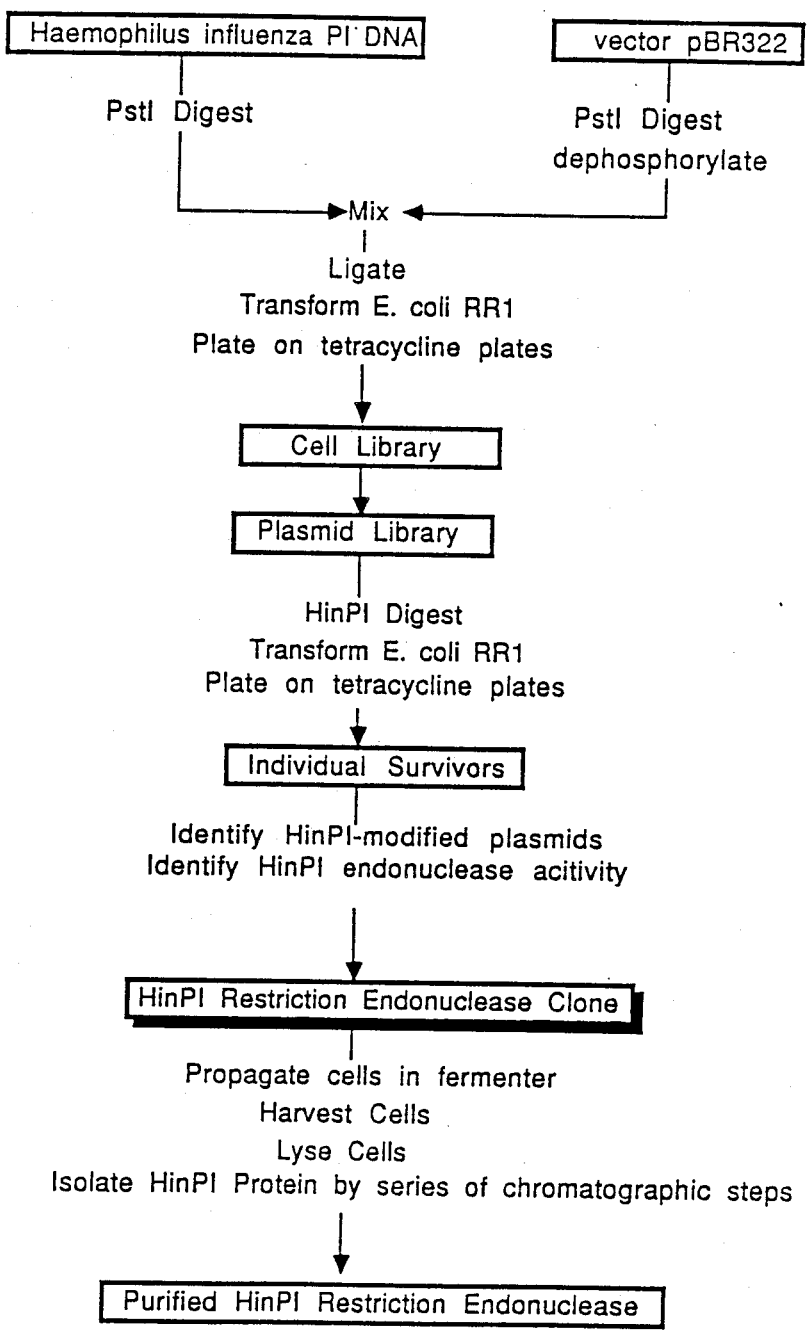
FIG. 1 illustrates the scheme for cloning and producing the HinPI restriction endonuclease.

The method described herein by which the HinPI restriction gene and methylase gene are preferably cloned and expressed are illustrated in FIG. 1, and they include the following steps:

1. The DNA of *Haemophilus influenza* P1 is purified. *H. influenza* P1 has been described by Shen et al., supra. Samples of this bacterium may be obtained from the American Type Culture Collection, catalog No. ATCC 53700.

2. The DNA is partially digested with a restriction endonuclease such as PstI.

3. The digested DNA is ligated to a cloning vector such as pBR322 (ATCC 37017) that contains one or more HinPI sites. The ligated DNA is used to transform an appropriate host such as *E. coli* strain RR1 (ATCC 31343).

4. The DNA/cell mixture is plated onto antibiotic media selective for transformed cells, such as tetracycline. After incubation, the transformed cell colonies are collected together into a single culture, the cell library.

5. The recombinant plasmids are purified in toto from the cell library to make the plasmid library.

6. The plasmid library is digested to completion with the HinPI restriction endonuclease, prepared from *H. Influenza* P1 by a method similar to that described in Shen et al., supra. HinPI digestion differentially destroys unmodified, non-methylase-containing, clones, increasing the relative frequency of HinPI methylase-carrying clones.

7. The digested plasmid library DNA is transformed back into an appropriate host such as *E. coli* strain RR1, and transformed colonies are again obtained by plating on antibiotic plates. The colonies are picked and their DNA is analyzed for the presence of the HinPI modification gene in the following manner: The plasmid DNA that they carry is purified and incubated in vitro with HinPI restriction endonuclease to determine whether it is resistant to digestion by HinPI. The total cellular DNA (chromosomal and plasmid) of the clone is also purified and incubated with HinPI restriction endonuclease. The DNA of clones that carry the HinPI methylase gene should be fully modified, and both the plasmid DNA and the total DNA should be found to be substantially, or completely resistant to digestion.

8. Clones carrying the HinPI restriction endonuclease are identified by preparing crude extracts of those clones identified in step 8 as carrying the HinPI methylase gene, and assaying the extracts for HinPI restriction endonuclease activity.

9. The HinPI restriction endonuclease may be produced from clones carrying the HinPI restriction and modification genes by propagation in a fermenter in a rich medium containing tetracycline. The cells are thereafter harvested by centrifugation and disrupted by sonication to produce a crude cell extract containing the HinPI restriction endonuclease activity.

10. The crude cell extract containing the HinPI restriction endonuclease activity is purified by standard protein purification techniques such as affinity-chromatography and ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE

Cloning of HinPI Restriction Endonuclease Gene

1. DNA purification: 10 g of frozen *Haemophilus influenza* P1 (ATCC53700) cells were thawed on ice for 1 hour then resuspended in 20 ml of 25% sucrose, 50mM Tris pH 8.0. 10 ml of 0.25M EDTA pH 8.0, and 6 ml of 10 mg/ml lysozyme in 0.25M Tris pH 8.0 were added. The suspension was kept on ice for 2 hours, then lysed by the addition of 24 ml of 1% Triton X-100, 50mM Tris pH 8.0, 67mM EDTA and 5 ml of 10% SDS. The solution was extracted with 70 ml of phenol, (previously equilibrated with 0.5M Tris pH 8.0), and 60 ml of Chloroform. The emulsion was centrifuged at 10K rpm for 30 minutes and the viscous upper layer was withdrawn and dialyzed against four changes of 10mM Tris pH 8.0, 1mM EDTA. The dialyzed solution was then digested with RNase at a final concentration of 100 ug/ml for 1 hour at 37° C. The DNA was then precipitated by adding NaCl to a final concentration of 0.4M, overlaying with 0.55 volumes of isopropyl alcohol, and spooling the DNA onto a glass rod by mixing the phases together. The DNA was resuspended in 10mM Tris pH 8.0, 1mM EDTA and stored at 4° C.

2. Digestion of DNA: The purified DNA was cleaved with PstI to achieve a range of digestion extents as follows: 80 ug of DNA was diluted into 800 ul of 10mM Tris pH 7.5, 10mM $MgCl_2$, 50mM NaCl, 10mM mercaptoethanol. The solution was divided into one 200 ul aliquot and six 100 ul aliquots. 20 units of PstI were added to the first, 200 ul, tube to achieve 1 unit of enzyme per ug of DNA. 100 ul was withdrawn from the first tube and transferred to the second tube to achieve 0.5 units/ug, and so on, each succeeding tube receiving half of the previous amount of PstI. The tubes were incubated at 37° C. for one hour, then heat-treated at 72° C. for 14 minutes and 10 ul from each was analyzed by agarose gel electrophoresis. The contents of all the tubes were combined and used as the source of digest fragments for cloning.

3. Ligation and transformation: 3 ug (30 ul) of PstI variably-digested *H. influenza* P1 DNA was mixed with 2 ug (20 ul) of PstI-cleaved and dephosphorylated pBR322 (ATCC 37017). 10 ul of 500mM Tris pH 7.5, 100mM $MgCl_2$, 100mM DTT, 5mM ATP, and 40 ul of sterile distilled water were added to bring the volume to 100 ul. 3.4 ul of T4 DNA ligase was added and the solution was incubated at 16° C. for 4 hours, then sterilized by extraction with 20 ul of chloroform. 80 ul of the ligated mixture was mixed with 1.0 ml of 50mM NaCl, 5mM $Na_3$ Citrate, 67mM $CaCl_2$ and 2.0 ml of ice-cold, competent *E. coli* RR1 (ATCC 31343) cells were added. The solution was incubated at 42° C. for 5 mins, then 8 ml of Luria-broth (L-broth) was added and incubation was continued at 37° C. for 4 hours.

4. Cell Library: The transformed cell culture was briefly centrifuged, the supernatant was discarded and the cells were resuspended in 1.0 ml of L-broth. 200 ul portions were plated onto Luria-agar (L-agar) plates containing 30 ug/ml tetracycline. After overnight incubation at 37° C., the plates were each flooded with 2.5 ml of 10mM Tris pH 7.5, 10mM $MgCl_2$ and the transformed colonies were scraped together and pooled.

5. Plasmid Library: 2.5 ml of the cell library was inoculated into 500 ml of L-broth containing 30 ug/ml tetracycline. The culture was shaken overnight at 37° C. then centrifuged at 4000 rpm for 5 minutes. The supernatant was discarded and the cell pellet was resuspended in 10 ml of 25% sucrose, 50mM Tris pH 8.0, at room temperature. 5 ml of 0.25M EDTA, pH 8.0, and 3 ml of 10 mg/ml lysozyme in 0.25M Tris, pH 8.0 were added. The solution was left on ice for 1 hour, then 12 ml of 1% Triton X-100, 50mM Tris pH 8.0, 67mM EDTA was forcefully pipetted in, and the suspension was gently swirled to achieve lysis.

The lysed mixture was transferred to a 50 ml tube and centrifuged for 45 min. at 17000 rpm, 4° C. The supernatant was removed with a pipette. 20.0 gm of solid CsCl was weighed into a 50 ml plastic screw-cap tube and 22.0 gm of supernatant was pipetted into the tube and mixed. 1.0 ml of 5 mg/ml ethidium bromide in 10mM Tris pH 8.0, 100mM NaCl, 1mM EDTA was added. The solution was transferred to two 5/8 in. × 3 in. centrifuge tubes and spun in a Beckman Ti70 rotor for 42 hours at 44000 rpm, 17° C. To collect the plasmids, the tubes were opened, illuminated with ultraviolet light, and the lower of the two fluorescent bands was collected by syringe. The lower band from each tube was combined and the ethidium bromide was removed by extracting four times with an equal volume of water-saturated, ice-cold N-Butanol.

The extracted solution was dialyzed against 4 changes of 10mM Tris pH 7.5, 1mM EDTA, then the nucleic acid was precipitated by the addition of 2 vols. of isopropanol and sufficient 5M NaCl to reach a final concentration of 0.4M. The solution was stored overnight at −20° C. then centrifuged for 15 min.at 15000 rpm, 0° C. The supernatant was discarded, the pellet was air-dried for 15 min. then dissolved in 500 ul of 10mM Tris pH 7.5, 1mM EDTA and stored at −20° C. The plasmid DNA concentration was found to be approximately 100 ug/ml.

6. Digestion of the Plasmid Library: The plasmid library was diluted to 30 ug/ml in HinPI restriction endonuclease digestion buffer (50mM Tris pH 7.5, 5mM $MgCl_2$, 0.5mM dithiothreitol). HinPI restriction endonuclease was added to a concentration of 32 units/ug DNA, and the tube was incubated at 37° C. for 1 hour. The reaction was terminated by heating to 72° C. for 12 minutes.

7. Transformation: 12.5 ul of the digested library was transformed into *E. coli* strain RR1, plated onto L-agar containing 30 ug/ml tetracycline and incubated overnight at 37° C. (sections 3 and 4). HinPI digestion reduced the number of transformants by a factor of $10^3$ compared to transformation with undigested plasmids. Twenty-nine individual colonies were picked and streaked onto duplicate plates, one containing 30 ug/ml tetracycline, the other containing 100 ug/ml ampicillin, to identify ampicillin-sensitive clones that had incorporated fragments. Fourteen of the 29 colonies were found to be ampicillin sensitive and each was inoculated into 10 ml of L-broth containing tetracycline, to prepare a miniculture, and streaked onto an L-agar plate containing tetracycline, to prepare a master stock.

8. Analysis of surviving individuals: fourteen of the tetracycline-resistant, ampicillin-sensitive colonies described in section 7 were grown in 10 ml cultures and the plasmids that they carried were prepared by the following miniprep purification procedure, adapted from the method of Birnboim and Doly (Nucleic Acids Res. 7: 1513 (1979)).

Miniprep Procedure: Each culture was centrifuged at 8000 rpm for 5 minutes; the supernatant was discarded and the cell pellet was resuspended in 1.0 ml of 25mM Tris, 10mM EDTA, 50mM glucose, pH 8.0, containing 1 mg/ml lysozyme. After 10 minutes at room temperature, 2.0 ml of 0.2M NaOH, 1% SDS was added to each tube and the tubes were shaken to lyse the cells, then placed on ice. Once the solutions had cleared, 1.5 ml of 3M sodium acetate, pH 4.8, was added to each and shaken. The precipitates that formed were spun down at 15000 rpm, 4° C. for 10 minutes. Each supernatant was poured into a centrifuge tube containing 3 ml of isopropanol and mixed. After 10 minutes at room temperature, the tubes were spun at 15000 rpm for 10 minutes to pellet the precipitated nucleic acids. The supernatants were discarded and the pellets were air-dried at room temperature for 30 minutes. Once dry, the pellets were resuspended in 850 ul of 10mM Tris, 1mM EDTA, pH 8.0. 75 ul of 5M NaCl was added to each and the solutions were transferred to Eppendorf tubes containing 575 ul of isopropanol, and again precipitated for 10 minutes at room temperature. The tubes were then spun for 45 seconds in a microfuge, the supernatants were discarded and the pellets were air-dried. The pellets were then dissolved in 500 ul of 10mM Tris, 1mM EDTA, pH 8.0, containing 100 ug/ml RNase and incubated for 1 hour at 37° C. to digest the RNA. The DNA was precipitated once more by the addition of 50 ul of 5M NaCl followed by 350 ul of isopropanol. After 10 minutes at room temperature, the DNA was spun down by centrifugation for 45 seconds, the supernatants were discarded and the pellets were redissolved in 150 ul of 10mM Tris 1mM EDTA, pH 8.0. The plasmid minipreps were subsequently analyzed by digestion with HinPI and PstI.

Figure 2:
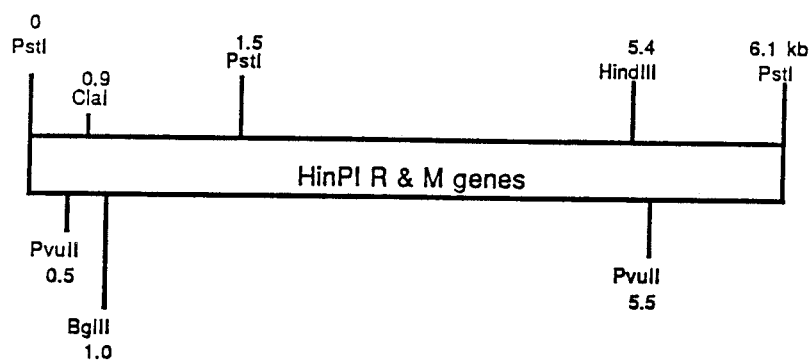
FIG. 2 is a restriction map of a 6.1 kb PstI multi-fragment of *H. influenza* P1 DNA encoding the HinPI restriction endonuclease and modification methylase that was inserted into the PstI site of pBR322 (ATCC 37017) to create pJB124RM 4-11 and pJB124RM 4-20.

9. HinPI Methylase Gene Clones: Twelve of the 14 plasmids that were analyzed were found to be sensitive to HinPI and to carry varied fragments of *H. influenza* P1 DNA. These plasmids were spurious survivors, and were discarded. The two remaining plasmids were found to be resistant to HinPI and to carry two PstI fragments of 4.6 and 1.5 kb in length (FIG. 2). These plasmids appeared to be identical; they were designated pJB124RM 4-11 and pJB124RM 4-20. Both were shown to carry not only the HinPI modification methylase gene but also the HinPI restriction endonuclease gene.

10. HinPI Restriction Gene Clone: pJB124RM 4-11, a sample of which has been deposited at the American Type Culture Collection under Accession No. 40776, pJB124RM 4-20 were found to carry the HinPI restriction endonuclease gene by assaying extracts prepared from *E.coli* RR1 carrying the plasmids.

The cell extract was prepared by growing a 50 ml culture overnight in L-broth plus 30 ug/ml tetracycline at 37° C. The cells were pelleted by centrifugation at 4K rpm for 5 min, the supernatant was discarded and the pellet was resuspended in 3 ml of sonication buffer (10mM Tris, pH 8.0, 10mM mercaptoethanol, 0.1mM EDTA). Once resuspended, 0.3 ml of sonication buffer containing 10 mg/ml lysozyme was added. The suspension was swirled and left on ice for 3 hours. The suspension was frozen overnight at −20° C. The frozen suspension was thawed on ice and 1 ml was transferred to an Eppendorf tube. 5 ul of 1% Triton X-100 was added, to achieve a final concentration of 0.005%, and mixed thoroughly. The mixture was microcentrifuged at 4° C. for 10 minutes and the supernatant was used as the cell extract.

Figure 3:
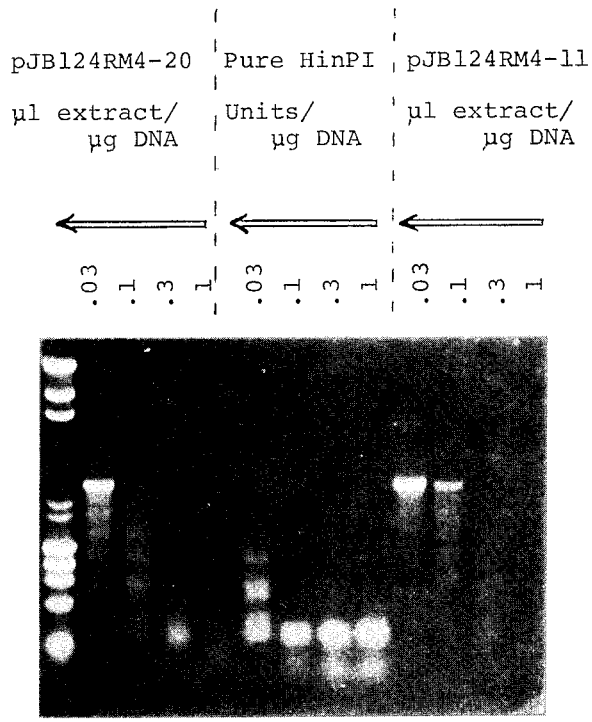
FIG. 3 is a photograph of an agarose gel illustrating HinPI restriction endonuclease activity in the crude extracts of *E. coli* RR1 (ATCC 31343) carrying pJB124RM 4-11 and pJB124RM 4-20.

25 ug of linear pUC19 DNA was diluted into 500 ul of HinPI restriction endonuclease digestion buffer (section 6). The solution was dispensed into 4 tubes, 150 ul into the first tube and 102.5 ul into each of the remaining 3 tubes. 7.5 ul of the cell extract was added to the first tube and mixed. 47.5 ul was removed from the first tube and transferred to the second tube, mixed and so on. The first tube thus received 1 ul of extract per ug of DNA, the second tube 0.3 ul/ug, the third tube 0.1 ul/ug and the fourth tube 0.03 ul/ug. The tubes, each containing 100 ul were incubated at 37° C. for one hour, then a 20 ul sample of each was analyzed by gel electrophoresis. The titre of the extract was found to be approximately 1000 units of HinPI restriction endonuclease per ml, which corresponds to about $1 \times 10^4$ units/gram of wet cell paste (FIG. 3).

What is claimed is:

1. Isolated DNA coding for the HinPI restriction endonuclease, wherein the isolated DNA is obtainable from the vector pJB124RM4-11.

2. A recombinant DNA vector comprising a vector into which a DNA segment coding for the HinPI endonuclease produced by *Haemophilus influenza* P1 ATCC No. 53700 has been inserted.

3. Isolated DNA coding for the HinPI restriction endonuclease and methylase, wherein the isolated DNA is obtainable from the vector pJB124RM4-11.

4. A cloning vector comprising the isolated DNA of claim 1.

5. A cloning vector comprising the isolated DNA of claim 3.

6. The cloning vector of claim 5, wherein the cloning vector comprises pJB124RM4-11.

7. A host cell transformed by the vector of claims 4, 5 or 6.

8. A method of cloning DNA coding for an HinPI restriction endonuclease comprising:
   (a) purifying DNA from *Haemophilus influenza* P1 ATCC No. 53700;
   (b) partially digesting the purified DNA with PstI to form DNA fragments;
   (c) ligating the DNA fragments into a cloning vector;
   (d) transforming a host cell with the cloning vector of step (c) to form a cell library;
   (e) purifying recombinant vectors from the cell library to form a plasmid library;
   (f) contacting the plasmid library of step (e) with HinPI to form a digestion pool, transforming the digestion pool into a host cell and plating onto tetracycline plates, and screening survivors which are ampicillin sensitive for the presence of one or more cloning vectors containing DNA coding for an HinPI methylase;
   (g) screening the cloning vector of step (f) which contains DNA coding for HinPI methylase for the presence of DNA coding for an HinPI restriction endonuclease; and
   (h) isolating the cloning vector of step (g) which contains DNA coding for HinPI restriction endonuclease.

9. A method of producing HinPI restriction endonuclease comprising culturing a host cell transformed with the vector of claim 4, 5 or 6 under conditions suitable for the expression of said endonuclease.

10. A method for producing HinPI restriction endonuclease:

(a) purifying DNA from *Haemophilus influenza* P1 ATCC No. 53700;
(b) partially digesting the purified DNA with PstI to form DNA fragments;
(c) ligating the DNA fragments into a cloning vector;
(d) transforming a host cell with the cloning vector of step (c) to form a cell library;
(e) purifying recombinant vectors from the cell library to form a plasmid library;
(f) contacting the plasmid library of step (e) with HinPI to form a digestion pool, transforming the digestion pool into a host cell and plating onto tetracycline plates, and screening survivors which are ampicillin sensitive for the presence of one or more cloning vectors containing DNA coding for a HinPI methylase;
(g) screening for cloning vector of step (f) which contains DNA coding for HinPI methylase for the presence of DNA coding for an HinPI restriction endonuclease;
(h) isolating the cloning vector of step (g) which contains DNA coding for the HinPI restriction endonuclease; and
(i) culturing a host cell transformed with the cloning vector of step (h) under conditions suitable for expression of the HinPI restriction endonuclease.

* * * * *

UNITED STATES PATENT AND TRADEMARK OFFICE
CERTIFICATE OF CORRECTION

PATENT NO. : 4,983,522

DATED : January 8, 1991

INVENTOR(S) : Janet M. Barsomian
Geoffrey G. Wilson

It is certified that error appears in the above-identified patent and that said Letters Patent is hereby corrected as shown below:

At column 7, line 51, change "Accession No. 40776" to read as --Accession No. 75170--.

Signed and Sealed this

First Day of June, 1993

Attest:

MICHAEL K. KIRK

*Attesting Officer*     *Acting Commissioner of Patents and Trademarks*